United States Patent [19]
Modak et al.

[11] Patent Number: 6,083,208
[45] Date of Patent: *Jul. 4, 2000

[54] TRICLOSAN-CONTAINING MEDICAL DEVICES

[75] Inventors: Shanta Modak, River Edge, N.J.; Sampath Lester, Nyack, N.Y.

[73] Assignee: The Trustees of Columbia University of the City of New York, New York, N.Y.

[ * ] Notice: This patent is subject to a terminal disclaimer.

[21] Appl. No.: 09/062,411

[22] Filed: Apr. 17, 1998

Related U.S. Application Data

[63] Continuation of application No. 08/583,239, Jan. 5, 1996, Pat. No. 5,772,640.

[51] Int. Cl.⁷ .................................................. A61M 25/00
[52] U.S. Cl. .............................. 604/265; 424/422; 623/1; 428/35.7
[58] Field of Search .................................... 604/264–265; 606/76; 428/35.7–36.9; 424/422; 623/1

[56] References Cited

U.S. PATENT DOCUMENTS

| | | |
|---|---|---|
| 4,605,564 | 8/1986 | Kulla et al. . |
| 4,723,950 | 2/1988 | Lee . |
| 4,994,047 | 2/1991 | Walker et al. . |
| 5,019,096 | 5/1991 | Fox, Jr. et al. . |
| 5,033,488 | 7/1991 | Curtis et al. . |
| 5,091,442 | 2/1992 | Milner . |
| 5,102,401 | 4/1992 | Lambert et al. . |
| 5,165,952 | 11/1992 | Soloman et al. . |
| 5,180,605 | 1/1993 | Milner . |
| 5,200,194 | 4/1993 | Edgren et al. . |
| 5,209,251 | 5/1993 | Curtis et al. . |
| 5,261,421 | 11/1993 | Milner . |
| 5,335,373 | 8/1994 | Dangman et al. . |
| 5,772,640 | 6/1998 | Modak et al. . |

FOREIGN PATENT DOCUMENTS 9302717  2/1993  WIPO .

OTHER PUBLICATIONS

The Merck Index, An Encyclopedia of Chemicals, Drugs, and Biologicals, Tenth Edition (Merck & Co., Inc. Rahway, NJ, 1983), p. 1092.

*Primary Examiner*—Mark Bockelman
*Attorney, Agent, or Firm*—Baker Botts L.L.P.

[57] ABSTRACT

The present invention relates to polymeric medical articles comprising the antiinfective agents chlorhexidine and triclosan. It is based, at least in part, on the discovery that the synergistic relationship between these compounds permits the use of relatively low levels of both agents, and on the discovery that effective antimicrobial activity may be achieved when these compounds are comprised in either hydrophilic or hydrophobic polymers.

16 Claims, No Drawings

TRICLOSAN-CONTAINING MEDICAL DEVICES

This application is a continuation of U.S. Ser. No. 08/583,239, filed Jan. 5, 1996, now U.S. Pat. No. 5,772,640.

SPECIFICATION

1. Introduction

The present invention relates to medical devices comprising synergistic combinations of triclosan and chlorhexidine.

2. Background of the Invention

Whenever a medical device comes in contact with a patient, a risk of infection is created. Thus, a contaminated examination glove, tongue depressor, or stethoscope could transmit infection. The risk of infection dramatically increases for invasive medical devices, such as intravenous catheters, arterial grafts, intrathecal or intracerebral shunts and prosthetic devices, which not only are, themselves, in intimate contact with body tissues and fluids, but also create a portal of entry for pathogens.

A number of methods for reducing the risk of infection have been developed which incorporate antiinfective agents into medical devices, none of which have been clinically proven to be completely satisfactory. Such devices desirably provide effective levels of antiinfective agent during the entire period that the device is being used. This sustained release may be problematic to achieve, in that a mechanism for dispersing antiinfective agent over a prolonged period of time may be required, and the incorporation of sufficient amounts of antiinfective agent may adversely affect the surface characteristics of the device. The difficulties encountered in providing effective antimicrobial protection increase with the development of drug-resistant pathogens.

One potential solution to these problems is the use of a synergistic combination of antiinfective agents that requires relatively low concentrations of individual antiinfective agents which may have differing patterns of bioavailability.

Two well-known antiinfective agents are chlorhexidine and triclosan. The following patents and patent application relate to the use of chlorhexidine and/or triclosan in medical devices.

U.S. Pat. No. 4,723,950 by Lee relates to a microbicidal tube which may be incorporated into the outlet tube of a urine drainage bag. The microbicidal tube is manufactured from polymeric materials capable of absorbing and releasing antimicrobial substances in a controllable sustained time release mechanism, activated upon contact with droplets of urine, thereby preventing the retrograde migration of infectious organisms into the drainage bag. The microbicidal tube may be produced by one of three processes: (1) a porous material, such as polypropylene, is impregnated with at least one microbicidal agent, and then coated with a hydrophilic polymer which swells upon contact with urine, causing the leaching out of the microbicidal agent; (2) a porous material, such as high density polyethylene, is impregnated with a hydrophilic polymer and at least one microbicidal agent; and (3) a polymer, such as silicone, is compounded and co-extruded with at least one microbicidal agent, and then coated with a hydrophilic polymer. A broad range of microbicidal agents are disclosed, including chlorhexidine and triclosan, and combinations thereof.

U.S. Pat. No. 5,091,442 by Milner relates to tubular articles, such as condoms and catheters, which are rendered antimicrobially effective by the incorporation of a non-ionic sparingly soluble antimicrobial agent, such as triclosan. The tubular articles are made of materials which include natural rubber, polyvinyl chloride and polyurethane. Antimicrobial agent may be distributed throughout the article, or in a coating thereon. A condom prepared from natural rubber latex containing 1% by weight of triclosan, then dipped in an aqueous solution of chlorhexidine, is disclosed. U.S. Pat. Nos. 5,180,605 and 5,261,421, both by Milner, relate to similar technology applied to gloves.

U.S. Pat. Nos. 5,033,488 and 5,209,251, both by Curtis et al., relate to dental floss prepared from expanded polytetrafluoroethylene (PTFE) and coated with microcrystalline wax. Antimicrobial agents such as chlorhexidine or triclosan may be incorporated into the coated floss.

U.S. Pat. No. 5,200,194 by Edgren et al. relates to an oral osmotic device comprising a thin semipermeable membrane wall surrounding a compartment housing a "beneficial agent" (that is at least somewhat soluble in saliva) and a fibrous support material composed of hydrophilic water-insoluble fibers. The patent lists a wide variety of "beneficial agents" which may be incorporated into the oral osmotic device, including chlorhexidine and triclosan.

U.S. Pat. No. 5,019,096 by Fox, Jr. et al. relates to infection-resistant medical devices comprising a synergistic combination of a silver salt (such as silver sulfadiazine) and chlorhexidine.

International Patent Application No. PCT/GB92/01481, Publication No. WO 93/02717, relates to an adhesive product comprising residues of a copolymerisable emulsifier comprising a medicament, which may be povidone iodine, triclosan, or chlorhexidine.

In contrast to the present invention, none of the above-cited references teach medical articles comprising synergistic combinations of chlorhexidine and triclosan which utilize relatively low levels of these agents and do not rely on the use of hydrophilic polymers to achieve effective levels of antimicrobial activity.

SUMMARY OF THE INVENTION

The present invention relates to polymeric medical articles comprising the antiinfective agents chlorhexidine and triclosan. It is based, at least in part, on the discovery that the synergistic relationship between these compounds permits the use of relatively low levels of both agents, and on the discovery that effective antimicrobial activity may be achieved when these compounds are comprised in either hydrophilic or hydrophobic polymers.

DETAILED DESCRIPTION OF THE INVENTION

The present invention relates to medical articles comprising synergistic combinations of chlorhexidine and triclosan.

Chlorhexidine may be provided by way of any form, salt or derivative thereof, including but not limited to chlorhexidine free base and chlorhexidine salts such as chlorhexidine diphosphanilate, chlorhexidine digluconate, chlorhexidine diacetate, chlorhexidine dihydrochloride, chlorhexidine dichloride, chlorhexidine dihydroiodide, chlorhexidine diperchlorate, chlorhexidine dinitrate, chlorhexidine sulfate, chlorhexidine sulfite, chlorhexidine thiosulfate, chlorhexidine di-acid phosphate, chlorhexidine difluorophosphate, chlorhexidine diformate, chlorhexidine dipropionate, chlorhexidine di-iodobutyrate, chlorhexidine di-n-valerate, chlorhexidine dicaproate, chlorhexidine malonate, chlorhexidine succinate, chlorhexidine malate, chlorhexidine tartrate, chlorhexidine dimonoglycolate, chlorhexidine monodiglycolate, chlorhexidine dilactate, chlorhexidine di-α-hydroxyisobutyrate, chlorhexidine diglucoheptonate, chlorhexidine di-isothionate, chlorhexidine dibenzoate, chlorhexidine dicinnamate, chlorhexidine dimandelate, chlorhexidine di-isophthalate, chlorhexidine di-2-hydroxynapthoate, and chlorhexidine embonate. The term "chlorhexidine", as used herein, may refer to any of such forms, derivatives, or salts, unless specified otherwise. Chlorhexidine salts may be solubilized using polyethylene glycol or propylene glycol, or other solvents known in the art.

The term triclosan refers to a compound also known as 2,4,4'-trichloro-2'-hydroxydiphenyl ether.

Medical articles that may be treated according to the invention include, but are not limited to, catheters including urinary catheters and vascular catheters (e.g. peripheral and central vascular catheters), wound drainage tubes, arterial grafts, soft tissue patches, gloves, shunts, stents, tracheal catheters, wound dressings, sutures and prosthetic devices (e.g. heart valves and LVADs).

The present invention provides, in various alternative nonlimiting embodiments, for: (1) compositions which provide a local concentration of chlorhexidine of between 100 and 2000 μg/ml and a local concentration of triclosan of between 250 and 2000 μg/ml; (2) treatment solutions of a polymer comprising between 1 and 5 percent, and preferably between 1.5 and 2.25 percent, of chlorhexidine; and between 0.5 and 5 percent, and preferably between 0.5 and 2 percent, of triclosan, wherein a medical article may be dipped or soaked in the polymer solution; (3) medical articles treated with a treatment solution as set forth in (2) above, and articles physically equivalent thereto (that is to say, articles prepared by a different method but having essentially the same elements in the same proportions); (4) treatment solutions of a polymer comprising between 1 and 5 percent, and preferably between 1.5 and 2.25 percent, of chlorhexidine; between 0.5 and 5 percent, and preferably between 0.5 and 2 percent, of triclosan; and between 0.5 and 1 percent (preferably 0.75 percent) of silver sulfadiazine, wherein a medical article may be dipped or soaked in the polymer solution; and (5) medical articles treated with a treatment solution set forth in (4) above, and articles physically equivalent thereto (that is to say, articles prepared by a different method but having essentially the same elements in the same proportions). Percentages recited herein refer to percent by weight, except as indicated otherwise.

In preferred embodiments, the ratio, by weight, of the total amount of antiinfective agent to polymer in the treatment solution is less than 1.5.

In one particular non-limiting embodiment, the present invention provides for a hydrophilic polymeric medical article (i.e., a medical article fabricated from a hydrophilic polymer) treated by dipping or soaking the article in a treatment solution of a hydrophilic polymer comprising chlorhexidine and triclosan wherein the chlorhexidine and triclosan are present in amounts such that their combination, in the treated article, has effective antimicrobial activity. The terms "treat", "treated", etc., as used herein, refer to coating, impregnating, or coating and impregnating a medical article with polymer/antiinfective agent. The term "hydrophilic polymer", as used herein, refers to polymers which have a water absorption greater than 0.6 percent by weight (and, in preferred embodiments, less than 2 percent by weight) including, but not limited to biomedical polyurethanes (e.g. ether-based polyurethanes and ester-based polyurethanes, as set forth in Baker, 1987, in *Controlled Release of Biologically Active Agents,* John Wiley and Sons, pp. 175–177 and Lelah and Cooper, 1986, *Polyurethanes in Medicine,* CRC Press, Inc., Fla. pp. 57–67), polylactic acid, polyglycolic acid, natural rubber latex, and gauze or water-absorbent fabric, including cotton gauze and silk suture material. In a specific, nonlimiting embodiment, the medical article is a polyurethane catheter which has been treated with (i.e., dipped or soaked in) a treatment solution comprising (i) between about 1 and 10 percent, preferably between about 2 and 6 percent, and more preferably about 3 percent, of a biomedical polyurethane; (ii) between 1 and 5 percent, and preferably between 1.5 and 2.25 percent, of chlorhexidine; and (iii) between 0.5 and 5 percent, and preferably between 0.5 and 2 percent, of triclosan. In related nonlimiting embodiments of the invention, the treatment solution may further comprise silver sulfadiazine, preferably in a concentration of between 0.5 and 1 percent (more preferably 0.75 percent). Section 6, below, presents working examples of embodiments set forth in this paragraph.

In another particular non-limiting embodiment, the present invention provides for a hydrophilic polymeric medical article treated by dipping or soaking the article in a treatment solution of a hydrophobic polymer comprising chlorhexidine and triclosan, wherein the chlorhexidine and triclosan are present in amounts such that their combination, in the treated article, has effective antimicrobial activity. The term "hydrophobic polymer", as used herein, refers to a polymer which has a water absorption of less than 0.6% and includes, but is not limited to, silicone polymers such as biomedical siicones (e.g., Silastic Type A) or elastomers (e.g., as set forth in Baker, 1987, in *Controlled Release of Biologically Active Agents,* John Wiley and Sons, pp. 156–162), Dacron, polytetrafluoroethylene (PTFE, also "Teflon"), polyvinyl chloride, cellulose acetate, polycarbonate, and copolymers such as silicone-polyurethane copolymers (e.g., PTUE 203 and PTUE 205 polyurethane-silicone interpenetrating polymer). In a specific, nonlimiting embodiment, the medical article is a polyurethane catheter which has been dipped or soaked in a treatment solution comprising (i) between about 1 and 10 percent, preferably between about 2 and 6 percent, and more preferably about 3 percent, of a polyurethane—silicone copolymer; (ii) between 1 and 5 percent, and preferably between 1.5 and 2.25 percent, of chlorhexidine; and (iii) between 0.5 and 5 percent, and preferably between 0.5 and 2 percent, of triclosan. In related nonlimiting embodiments of the invention, the treatment solution may further comprise silver sulfadiazine, preferably in a concentration of between 0.5 and 1 percent (more preferably 0.75 percent). Section 7, below, presents working examples of embodiments set forth in this paragraph.

In another particular non-limiting embodiment, the present invention provides for a hydrophobic polymeric medical article treated by dipping or soaking the article in a treatment solution of hydrophobic polymer comprising chlorhexidine and triclosan, wherein the chlorhexidine and triclosan are present in amounts such that their combination, in the treated article, has effective antimicrobial activity. In a specific, nonlimiting embodiment, the medical article is a silicone catheter which has been dipped or soaked in a treatment solution comprising (i) between about 1 and 10 percent, and preferably about 5 percent, of a silicone polymer; (ii) between 1 and 5 percent, and preferably between 1.5 and 2.25 percent, of chlorhexidine; and (iii) between 0.5 and 5 percent, and preferably between 0.5 and 2 percent, of triclosan. In related nonlimiting embodiments of the invention, the treatment solution may further comprise silver sulfadiazine, preferably in a concentration of between 0.5 and 1 percent (more preferably 0.75 percent). In still other related embodiments a coating of a hydrophobic polymer may be applied over the treated article. Section 8, below, presents working examples of embodiments set forth in this paragraph.

In another particular non-limiting embodiment, the present invention provides for a hydrophobic polymeric medical article treated by dipping or soaking the article in a treatment solution of hydrophilic polymer comprising chlorhexidine and triclosan, wherein the chlorhexidine and triclosan are present in amounts such that their combination, in the treated article, has effective antimicrobial activity. In a specific, nonlimiting embodiment, the medical article is a silicone catheter or Teflon graft which has been dipped or soaked in a treatment solution comprising (i) between about 1 and 10 percent, preferably between about 2 and 6 percent, and more preferably about 3 percent, of a biomedical polyurethane polymer; (ii) between 1 and 5 percent, and preferably between 1.5 and 2.25 percent, of chlorhexidine; and (iii) between 0.5 and 5 percent, and preferably between 0.5 and 2 percent, of triclosan. In related nonlimiting embodiments of the invention, the treatment solution may further comprise silver sulfadiazine, preferably in a concentration of between 0.5 and 1 percent (more preferably 0.75 percent).

Successful treatment of a medical article with a polymer comprising an antiinfective agent may be problematic, particularly where the medical article has a hydrophobic surface. The adherence of the polymer may depend upon (1) the polymeric matrix in which the antiinfective agent is suspended; (2) compatibility (or lack thereof) between the agent-polymeric matrix and the surface of the article; (3) the solvent system; and (4) the thickness of polymer/antiinfective agent desirably applied. Furthermore, the rates of release of various antiinfective agents from diverse polymers may differ. For example, the rate of release of chlorhexidine from a silicone matrix is faster than the rate of release of silver sulfadiazine from the same matrix. In order to compensate for this difference, one potential solution would be to increase the amounts of chlorhexidine and silver sulfadiazine in the matrix. Unfortunately, polymers comprising high levels of chlorhexidine and silver sulfadiazine have been found to adhere poorly to silicone catheters. In order to provide an alternative solution to the problem, two different methods for treating medical articles have been developed: a one step method, and a two-step method, both of which are set forth below.

According to the one-step method of the invention, a polymeric medical article may be treated with a solution comprising one or more antiinfective agent and a biomedical polymer dissolved in one or more solvents, wherein the solvent(s) selected are capable of swelling the polymeric medical article to be treated; such a solution is referred to herein as an "impregnating solution", and the process by which the article is treated with antiinfective agent is referred to as "impregnation". Suitable solvents include, but are not limited to, tetrahydrofuran ("THF"), dichloromethane, carbon tetrachloride, methanol, ethanol, methyl ethyl ketone, heptane, and hexane, and mixtures thereof. The biomedical polymer may be hydrophilic or hydrophobic, and includes the various polymers set forth above.

If a hydrophilic polymeric medical article is to be impregnated with chlorhexidine and triclosan, the impregnating solution may, in specific nonlimiting embodiments, comprise the following (percentages of solvents in this paragraph being volume/volume): (1) 95% ethanol; (2) 70% ethanol/30% water; (3) 50% ethanol/50% water; or (4) 30% reagent alcohol/70% THF containing 2–3% of a biomedical polyurethane. For specific examples, see Section 14, below. Preferred soaking times vary between 5 minutes and 1 hour.

If a hydrophobic polymeric medical article is to be impregnated with chlorhexidine and triclosan, the impregnating solution may, in specific nonlimiting embodiments, comprise the following (percentages of solvents in this paragraph being volume/volume): (1) 10% methanol/90% THF; (2) 10% ethanol/90% THF; (3) 30% methanol/70% THF; (4) 30% ethanol/70% THF; (5) 1–5 percent silicone polymer in 10% methanol/90% THF; (6) 1–5 percent silicone polymer in 10% ethanol/90% THF; (7) 1–2 percent polylactic acid in 10% methanol/90% THF; (8) 1–2 percent polylactic acid in 10% ethanol/90% THF; (9) 1–5 percent silicone polymer in 30% methanol/70% THF; (10) 1–5 percent silicone polymer in 30% ethanol/70% THF; (11) 1–2 percent polylactic acid in 30% methanol/70% THF; (12) 1–2 percent polylactic acid in 30% ethanol/70% THF; (13) 1–5 percent silicone polymer in 100% methyl ethyl ketone; and (14) 1–2 percent polyurethane in 30% ethanol/70% THF. For specific examples, see Section 15, below.

The impregnating solution preferably comprises between 0.2 and 10 percent antiinfective agent and between 0.5 and 4 percent biomedical polymer. The medical article, or a portion thereof, may be immersed in the impregnating solution to swell, after which the article may be removed and dried at room temperature until all solvent has evaporated and the article is no longer swollen. During the swelling process, antiinfective agent and small amounts of polymer may be distributed within the polymeric substrate of the article; during drying, the antiinfective agent and biomedical polymer may migrate somewhat toward the surface of the article. After drying, the article may be rinsed in either water or alcohol and wiped to remove any excess antiinfective agent and/or polymer at the surface. This may leave a sufficient amount of antiinfective agent just below the surface of the article, thereby permitting sustained release of the agent over a prolonged period of time. Antiinfective agents which may be incorporated by this process include but are not limited to chlorhexidine, triclosan, silver sulfadiazine, parachlorometaxylene, benzalkonium chloride, bacitracin, polymyxin, miconasole and rifampicin, as well as combinations thereof. In preferred, nonlimiting embodiments of the invention, synergistic combinations of chlorhexidine and triclosan may be dissolved in a mixture of methanol and tetrahydrofuran to produce an impregnating solution that may be used to render a silicone catheter antiinfective. In a specific, nonlimiting example, the amount of chlorhexidine may be between 1 and 5 percent and preferably between 1.5 and 2.25 percent of the impregnating solution, and the amount of triclosan may be between 0.5 and 5 percent, and preferably between 0.5 and 2 percent. The resulting impregnating solution may further contain between 1 and 10 percent and preferably between 2 and 4 percent of a biomedical polymer such as a silicone polymer (e.g., Silastic Type A) or polycaprolactone. Specific examples of the one-step method are provided in Section 12 below.

According to the two-step method of the invention, the one-step method may be used to impregnate a medical article with antiinfective agent, and then the medical article may be dipped into a polymeric solution and dried. This method forms a polymeric coating on the article and further controls the rate of release of antiinfective agent. When the two step method is practiced, the biomedical polymer may be omitted from the first soaking step. An antiinfective agent may further be comprised in the polymeric coating. In a specific, nonlimiting example, a silicone catheter may be dipped in a mixture of methanol and tetrahydrofuran containing between about 1 and 5 percent, and preferably between 1.5 and 2.25 percent, of chlorhexidine; between 0.5 and 5 percent and preferably between 0.5 and 2 percent of triclosan; and between 1 and 10 percent, and preferably between 2 and 4 percent, of a biomedical polymer (preferably a silicone polymer such as Silastic Type A) for about 30 minutes, dried, and then dipped in a higher concentration (but less than 10 percent) of biomedical polymer dissolved in a suitable solvent. For example, but not by way of limitation, a coating may be applied using a solution of 30% ethanol/70% THF containing 2–3 percent of a biomedical polyurethane, or a solution of 1–5 percent of Silastic Type A. An example of this method is set forth in Section 8, below.

Antiinfective medical articles prepared by other methods (e.g., extrusion, casting) but being otherwise substantially the same as articles produced by dipping or soaking, are within the scope of the claimed invention.

5. EXAMPLE

Combinations of Chlorhexidine and Triclosan Exhibit Synergistic Activity in Bacterial Cultures Various concentrations of chlorhexidine diacetate ("CHA") and/or triclosan ("TC") were dispensed in 1.0 ml trypticase soy broth ("TSB") containing 20 percent bovine calf serum("BCS") and inoculated with $10^7$ colony-forming units ("CFU") of *Staphylococcus aureus*. After one minute, the cultures were diluted with drug-inactivating medium (1:100 dilution in LTSB drug inactivating medium, which is 5% Tween 80, 2% lecithin, 0.6% sodium oleate, 0.5% sodium thiosulfate, 0.1% protease peptone and 0.1% tryptone) and 0.2 ml of the diluted culture was subcultured on a trypticase soy agar plate for the determination of colony counts. The results, shown in Table I, demonstrate the synergistic activity of combinations of chlorhexidine and triclosan. For example, whereas 500 micrograms per milliliter of CHA causes an approximately 17-fold decrease in CFU, and 500 micrograms per milliliter of triclosan causes an approximately 2400-fold decrease, the combination of these agents is associated with zero CFU, an at least $1\times10^7$-fold decrease.

TABLE I

| Antiinfective Agent | Concentration (μg/ml) | CFU/ml (1 minute kill) |
|---|---|---|
| CHA | 2000 | $2.1 \times 10^3$ |
| CHA | 1000 | $5.0 \times 10^4$ |
| CHA | 500 | $6.0 \times 10^5$ |
| TC | 500 | $4.2 \times 10^3$ |
| TC | 250 | $2.0 \times 10^5$ |
| CHA + TC | 2000 + 500 | 0 |
| CHA + TC | 2000 + 250 | 0 |
| CHA + TC | 1000 + 250 | 0 |
| CHA + TC | 500 + 500 | 0 |
| CONTROL | | $1.0 \times 10^7$ |

6. EXAMPLE

Combinations of Chlorhexidine and Triclosan are More Effective Than Combinations of Chlorhexidine and Silver Sulfadiazine When Applied to Hydrophilic Catheters Polyurethane central venous catheters fabricated Of Tecoflex 93-A polyurethane were dipped in solutions containing 3 percent of a biomedical polyurethane (Tecoflex 93-A; "PU") and CHA, TC and/or silver sulfadiazine ("AgSD") dissolved in 30 percent ethanol and 70 percent tetrahydrofuran ("THF") (v/v) and air-dried. Bacterial adherence on these catheters was measured as follows. A 2 cm segment of dipped catheter was suspended in 3 ml TSB containing 10 percent BCS and incubated in a water bath shaker at 37° C. The media was changed daily. After 2 days the catheter segments were removed and transferred to fresh media containing $10^6$ CFU/ml of *Staphylococcus aureus* and incubated for 24 hours. The segments were removed, rinsed with saline, and then suspended in LTSB drug-inactivating medium and sonicated for 20 minutes to remove the adherent bacteria. Aliquots from the LTSB extract were then subcultured on trypticase soy agar plates to determine colony counts. The results are presented in Table II, and demonstrate that combinations of CHA and TC are superior in preventing bacterial adherence when compared with CHA alone or in combination with AgSD.

TABLE II

| Coating | Adherent Bacteria (CFU/ml) |
|---|---|
| 3% PU + 2.5% CHA | $5 \times 10^4$ |
| 3% PU + 1.5% CHA + 0.75% AgSD | $2 \times 10^4$ |
| 3% PU + 1.5% CHA + 1% TC | 5 |
| 3% PU + 1.5% CHA + 0.75% AgSD + 1% TC | 40 |

In additional experiments, addition segments of the same type of polyurethane catheters coated with CHA, TC and/or AgSD were tested for the ability to produce zones of inhibition in trypticase soy agar plates seeded with 0.3 ml of $10^6$ CFU of *Staphylococcus aureus, Enterobacter cloacae, Candida albicans,* and *Pseudomonas aeruginosa*. The coated catheter segments were placed vertically on the seeded plates, which were then incubated for 24 hours at 37° C. before the zones of inhibition were measured. The results, shown in Table III, demonstrate the superior effectiveness of mixtures of chlorhexidine and triclosan.

TABLE III

| | Zone Of Inhibition (mm) Coating*: | | | |
|---|---|---|---|---|
| Organism | A | B | C | D |
| S. aureus | 14.5 | 15.0 | 13.0 | 16.5 |
| E. cloacae | 9.0 | 12.0 | 7.5 | 3.0 |
| C. albicans | 12.0 | 12.0 | 11.5 | 0 |
| P. aeruginosa | 12.5 | 12.5 | 12.0 | 0 |

*coating A = 3% PU + 2.25% CHA
coating B = 3% PU + 1.75% CHA + 0.5% TC
coating C = 3% PU + 1.75% CHA + 0.5% AgSD
coating D = 3% PU + 0.5% AgSD + 1.75% TC

7. EXAMPLE

Hydrophilic Catheters Coated With Hydrophobic Polymer Comprising Chlorhexidine and Triclosan Have Antimicrobial Activity The antimicrobial effectiveness of polyurethane central venous catheters (fabricated from Tecoflex 93-A polyurethane) coated with chlorhexidine diacetate and either triclosan or silver sulfadiazine in two polymeric coatings of differing water absorption were tested. The polymeric coatings, applied as set forth in Section 6 above, comprised either polyurethane 93A ("PU 93A"), a hydrophilic polyurethane having a water absorption of about 1–2 percent or polyurethane-silicone interpenetrating polymer ("PTUE 205") a hydrophobic silicone-polyurethane copolymer having a water absorption of only 0.4%. Antibacterial activity was measured by zones of inhibition, using methods as set forth in Section 6, above. The results, as regards antibacterial activity toward Staphylococcus aureus, Enterobacter cloacae, and Candida albicans at days 1 and 3 of culture, are shown in Tables IV, V and VI, respectively, and demonstrate that combinations of chlorhexidine diacetate and triclosan were effective when comprised in hydrophilic (PU 93A) as well as hydrophobic (PTUE 205) coatings.

TABLE IV

Antibacterial Activity Against S. aureus

| Coating | Zone of Inhibition (mm) | |
|---|---|---|
| | Day 1 | Day 3 |
| 3% PTUE 205 + 1.5% CHA + 1.5% TC | 16.0 | 11.0 |
| 3% PTUE 205 2% CHA + 0.75% AgSD | 14.5 | 11.0 |
| 3% PU 93A + 1.5% CHA + 1.5% TC | 16.0 | 11.5 |
| 3% PU 93A + 2% CHA + 0.75% AgSD | 14.5 | 11.0 |

TABLE V

Antibacterial Activity Against E. cloacae

| Coating | Zone of Inhibition (mm) | |
|---|---|---|
| | Day 1 | Day 3 |
| 3% PTUE 205 + 1.5% CHA + 1.5% TC | 12.0 | 6.0 |
| 3% PTUE 205 2% CHA + 0.75% AgSD | 8.5 | 0 |
| 3% PU 93A + 1.5% CHA + 1.5% TC | 11.0 | 7.0 |
| 3% PU 93A + 2% CHA + 0.75% AgSD | 7.0 | 0 |

TABLE VI

Antibacterial Activity Against C. albicans

| Coating | Zone of Inhibition (mm) | |
|---|---|---|
| | Day 1 | Day 3 |
| 3% PTUE 205 + 1.5% CHA + 1.5% TC | 11.0 | 7.0 |
| 3% PTUE 205 2% CHA + 0.75% AgSD | 12.0 | 9.5 |
| 3% PU 93A + 1.5% CHA + 1.5% TC | 12.5 | 7.0 |
| 3% PU 93A + 2% CHA + 0.75% AgSD | 10.0 | 6.5 |

8. EXAMPLE

Hydrophobic Catheters Treated With Hydrophobic Polymer Comprising Chlorhexidine and Triclosan Have Antimicrobial Activity Silicone central venous catheters fabricated from Dow Corning Q7-4765A silicone polymer or Q7-4765B silicone polymer were used to determine the effectiveness of impregnation with hydrophobic polymers comprising chlorhexidine diacetate and triclosan on hydrophobic substrates. The silicone catheters were soaked for about 30 minutes in a solution of 5 percent methanol and 95 percent THF (v/v) comprising (i) 2 percent medical adhesive Silastic Type A and (ii) chlorhexidine diacetate and either triclosan or silver sulfadiazine. The dipped catheters were dried and then dipped in a solution of 5 percent methanol and 95 percent THF (v/v) containing 5 percent Silastic Type A ("SilA"), and dried again. The catheter segments were then tested for the production of zones of inhibition on trypticase soy agar plates inoculated with S. aureus or E. cloacae. The results are presented in Table VII.

TABLE VII

| Treatment | Zone Of Inhibition (mm) | |
|---|---|---|
| | S. aureus | E. cloacae |
| 2% SilA + 1.5% CHA + 0.5% TC, then 5% SilA | >50 | 21 |
| 2% SilA + 1.5% CHA + 0.5% AgSD, then 5% SilA | 17 | 15 |

9. EXAMPLE

Triclosan Exhibits Prolonged Release From Polymer Coatings

Silicone central venous catheters fabricated from Dow Corning Q7-4765A silicone polymer or Q7-4765B silicone polymer were treated as set forth in Section 8, above, and then, immediately after drying, were extracted in dichloromethane/methanol/water (50%/25%/25%, v/v) in order to determine the amount of agent contained in the catheter segment tested (i.e., the uptake). To determine the rate of drug release, catheter segments were suspended in saline and incubated at 37° C. for up to seven days; the saline was collected and replaced with fresh saline on the first day and every 48 hours thereafter, and the amount of drug present in the collected saline was measured. The results are presented in Table VIII.

TABLE VIII

| Treatment | Uptake ($\mu$g/cm) | Release ($\mu$g/cm) | | | |
|---|---|---|---|---|---|
| | | Day 1 | Day 3 | Day 5 | Day 7 |
| 2% SilA + 2% CHA, then 5% SilA | 60 | 28.0 | 4.1 | 3.1 | 2.6 |
| 2% SilA + 2% TC, then 5% SilA | 1168 | 10.0 | 9.5 | 11.1 | 11.4 |

Silicone catheters impregnated with Silastic Type A comprising either 2% triclosan or 2% chlorhexidine diacetate were then tested for the ability to produce zones of inhibition on trypticase soy agar plates inoculated with S. aureus, E. cloacae, C. albicans, or P. aeruginosa. The results of these experiments are shown in Table IX, and demonstrate that when higher concentrations of triclosan or chlorhexidine diacetate alone were used, triclosan-treated catheters were found to be equally or more effective than CHA-treated catheters.

TABLE IX

| | Zones Of Inhibition (mm) Treatments: | | | |
|---|---|---|---|---|
| | 2% SilA + 2% CHA, then 5% SilA | | 2% SilA + 2% TC, then 5% SilA | |
| Organism | Day 1 | Day 3 | Day 1 | Day 3 |
| S. aureus | 17.5 | 16.0 | >50 | >50 |
| E. cloacae | 15.0 | 9.0 | 40.0 | 40.0 |
| C. albicans | 13.5 | 6.0 | 13.0 | 13.0 |
| P. aeruginosa | 13.0 | 0 | 8.5 | 0 |

10. EXAMPLE

Uptake of Chlorhexidine and Triclosan in PTFE Grafts

Arterial grafts fabricated from polytetrafluoroethylene ("PTFE") were cut into segments and impregnated with Silastic Type A comprising chlorhexidine diacetate or triclosan in 30% methanol/70% THF (v/v), in proportions set forth below. The treated grafts were then extracted with dichloromethane/methanol/water (50%/25%/25%, v/v), and the amounts of solubilized antiinfective agents were determined. Table X shows the uptake of agent by the treated grafts.

TABLE X

| Treatment | Agent Uptake (µg/cm) |
|---|---|
| 2% SilA + 2% CHA | 895 |
| 2% SilA + 2% TC | 2435 |

11. EXAMPLE

Antimicrobial Effectiveness of Medical Articles Fabricated From Teflon, Dacron or Natural Rubber Latex and Impregnated With Combinations of Chlorhexidine and Triclosan Chlorhexidine diacetate and either triclosan or silver sulfadiazine, in proportions set forth below, were dissolved in 5% methanol/95% THF (v/v). Segments of Dacron grafts, PTFE grafts, and natural rubber latex urinary catheters were then soaked in the resulting solutions for 15 minutes to impregnate the segments with antiinfective agents. This procedure allows the polymer substrates of the devices to incorporate antiinfective agent. The segments were then removed from the soaking solution, dried, rinsed with water, and wiped. The ability of the treated segments to produce zones of inhibition on trypticase soy agar plates inoculated with S. aureus and E. cloacae was then tested. The results, shown in Tables XI–XIII, demonstrate that the combination of chlorhexidine and triclosan produced superior antimicrobial results compared to the combination of chlorhexidine and silver sulfadiazine.

TABLE XI

| PTFE Graft | | |
|---|---|---|
| | Zone Of Inhibition (mm) | |
| Impregnating Solution | S. aureus | E. cloacae |
| 5% CHA + 0.5% TC | 37.0 | 22.0 |
| 1.5% CHA + 0.75% AgSD | 22.0 | 16.5 |

TABLE XII

| Dacron Graft | | |
|---|---|---|
| | Zone Of Inhibition (mm) | |
| Impregnating Solution | S. aureus | E. cloacae |
| 5% CHA + 0.5% TC | >40 | 30.0 |
| 1.5% CHA + 0.75% AgSD | 26.0 | 27.0 |

TABLE XIII

| Latex Catheter | | |
|---|---|---|
| | Zone Of Inhibition (mm) | |
| Impregnating Solution | S. aureus | E. cloacae |
| 5% CHA + 0.5% TC | 26.0 | 20.0 |
| 1.5% CHA + 0.75% AgSD | 18.0 | 12.0 |

12. EXAMPLE

Antimicrobial Effectiveness of Silicone Catheters Prepared by a One-Step Impregnation Method Silicone catheters, as used in Example 8, were prepared by a one-step impregnation method as follows. Segments of the silicone catheters were soaked for about 30 minutes in impregnating solutions of 90% THF/10% methanol (v/v) containing 2% Silastic Type A, chlorhexidine, and either silver sulfadiazine or triclosan. The segments were then dried, and tested for their ability to produce zones of inhibition (at one and three days) in trypticase soy agar plates inoculated with S. aureus, E. cloacae, C. albicans, and P. aeruginosa. The results, presented in Table XIV, demonstrate the effectiveness of chlorhexidine and triclosan-impregnated catheters.

TABLE XIV

| | Zones Of Inhibition (mm) Treatments: | | | |
|---|---|---|---|---|
| | 2% SilA + 1.5% CHA + 0.5% TC | | 2% SilA + 1.5% CHA + 0.5% AgSD | |
| Organism | Day 1 | Day 3 | Day 1 | Day 3 |
| S. aureus | >40 | 39 | 17.5 | 13.5 |
| E. cloacae | 21 | 21 | 15 | 8 |
| C. albicans | 13.5 | 7 | 13.5 | 6 |
| P. aeruginosa | 13.5 | 6.5 | 13 | 0 |

Additional formulations of impregnating solutions were tested for their ability to render the same type of silicone catheter segments antiinfective against C. albicans, the microorganism which appeared to be inhibited only by relatively high amounts of antiinfective agent. The following impregnating solutions comprised chlorhexidine, triclosan and either Silastic Type A, polycaprolactone, or no polymer in a 5% methanol/95% THF solvent. Table XV shows that when both polymer and antiinfective agent were comprised in the impregnating solution, higher antiinfective activity was achieved.

TABLE XV

| Impregnating Solution | Zone Of Inhibition (mm) |
|---|---|
| 4% SilA + 5% CHA + 1% TC | 12.0 |
| 1% polycaprolactone + 5% CHA + 1% TC | 12.0 |
| No polymer, 5% CHA + 1% TC | 6.5 |

13. EXAMPLE

Diffusion of Antiinfective Agents From Medical Articles Treated With Impregnating Solutions With and Without Polymer The following impregnating solutions, "A" and "B", were used to impregnate segments of Dacron and PTFE grafts. The treated grafts were then rinsed with saline, and the amounts of antiinfective agent incorporated into the grafts were determined, before and after rinsing, by extraction of antiinfective agent with dichloromethane/methanol/water (50%/25%/25%, v/v). The results, set forth in Table XVI, demonstrate that the addition of a polymer to the impregnating solution produces a treated medical article which exhibits greater retention of antiinfective agent.

| Solution A: | 1% polycaprolactone + 0.1% CHA + 0.02% TC, in 5% methanol/95% THF (v/v) |
|---|---|
| Solution B: | 0.1% CHA + 0.02% TC, in 5% methanol/95% THF (v/v) |

TABLE XVI

| | Drug Levels ($\mu$g/cm) | | | |
|---|---|---|---|---|
| | Dacron Graft | | PTFE Graft | |
| Solution: | A | B | A | B |
| Solution A | | | | |
| Before rinsing | 392 | 548 | 73 | 90 |
| After rinsing | 353 | 547 | 56 | 88 |
| Solution B | | | | |
| Before Rinsing | 409 | 573 | 50 | 44 |
| After rinsing | 132 | 553 | 24 | 44 |

14. EXAMPLE

Drug Uptake and Release by Hydrophilic Catheters Impregnated With Chlorhexidine or Triclosan Polyurethane central venous catheter segments fabricated of Tecoflex 93-A polyurethane were impregnated with solutions "C", "D", "E", "F" and "G" set forth below by soaking the catheter segments for about two minutes followed by drying and rinsing with water. Drug uptake was measured by extracting the impregnated catheter segments with dichloromethane/methanol/water (50%/25%/25% v/v).

Drug release was measured over a period of six days by suspending the catheter segments in saline (one 2 cm segment in 2 ml saline), and agitated in a heated water bath at 37° C.; the saline was changed daily and drug release was measured as described above. The results are shown in Table XVII. Polyurethane, as set forth below, is Tecoflex 93-A polyurethane.

| Solution C: | 3% polyurethane + 3% CHA in 30% reagent alcohol/70% THF |
|---|---|
| Solution D: | 3% polyurethane + 3% TC in 30% reagent alcohol/70% THF |
| Solution E: | 3% polyurethane + 2% CHA + 2% TC, in 30% reagent alcohol/70% THF |
| Solution F: | 2% CHA in 95% ethanol |
| Solution G: | 3% CHA + 1% TC in 95% ethanol |

TABLE XVII

| Solution | Drug | Uptake ($\mu$g/cm) | Drug Release ($\mu$g/cm) Day No. | | | | | |
|---|---|---|---|---|---|---|---|---|
| | | | 1 | 2 | 3 | 4 | 5 | 6 |
| C | CHA | 197 | 78 | 36 | 20 | 2.6 | 0.8 | 0.8 |
| D | TC | 300 | 0.4 | .13 | 0.1 | 0.1 | 0.1 | 0.1 |
| E | CHA | 202 | 66 | 16.8 | 7.0 | 5.0 | 5.0 | 5.0 |
|   | TC | 230 | 0.4 | 0.3 | <.1 | <.1 | <.1 | <.1 |
| F | CHA | 254 | 15 | 9.6 | 7.8 | 2.5 | 2.5 | 2.5 |
| G | CHA | 223 | 7.1 | 3.5 | 3.0 | 0.8 | 0.8 | 0.8 |
|   | TC | 368 | <.1 | <.1 | <.1 | <.1 | <.1 | <.1 |

15. EXAMPLE

Release of Chlorhexidine and Triclosan From Impregnated Silicone Catheter Segments Segments of silicone central venous catheters fabricated from Dow Corning Q7-4765A silicone polymer or Q7-4765B silicone polymer were impregnated with either solution H or I by soaking for 30 minutes, and then the release of drug was measured daily by methods set forth above. The results of these measurements are presented in Table XVIII.

Solution H: 2% SilA+5% CHA in 10% methanol/90% THF (v/v)

Solution I: 2% SilA+5% CHA+2% TC in 10% methanol/90% THF (v/v)

TABLE XVIII

| Solution | Drug | Daily Release ($\mu$g/cm) | | | | |
|---|---|---|---|---|---|---|
| | | Day 1 | Day 2 | Day 3 | Day 4 | Day 5 |
| H | CHA | 2.7 | 1.0 | 0.6 | 0.9 | 0.9 |
| I | CHA | 0.8 | 0.9 | 0.6 | 0.8 | 0.8 |
|   | TC | 2.6 | 5.6 | 2.3 | 1.5 | 1.5 |

Various publications are cited herein, which are hereby incorporated by reference in their entireties.

What is claimed is:

1. A hydrophilic polymeric medical article having a coating resulting from dipping or soaking the article in a treatment solution comprising between about 2 and 6 percent by weight of a biomedical polyurethane; between 0.5 and 2 percent by weight of triclosan; between 0.5 and 1 percent by weight of silver sulfadiazine; and between 1.5 and 2 percent by weight of an antiinfective agent selected from the group consisting of chlorhexidine free base, a chlorhexidine salt, and a chlorhexidine derivative.

2. The medical article of claim 1 which is a catheter.

3. The catheter of claim 2 which is an intravenous catheter.

4. The catheter of claim 3 which is fabricated from a biomedical polyurethane.

5. The catheter of claim 4 wherein the hydrophilic polymer in the coating is a biomedical polyurethane.

6. A hydrophobic polymeric medical article treated with a treatment solution comprising between about 1 and 10 percent by weight of a silicone polymer; between 0.5 and 2 percent by weight of triclosan; and between 1.5 and 2.25 percent by weight of an antiinfective agent selected from the group consisting of chlorhexidine free base, a chlorhexidine salt, and a chlorhexidine derivative.

7. The medical article of claim 6, further comprising silver sulfadiazine.

8. The medical article of claim 7 wherein the medical article is fabricated from a hydrophobic polymer selected from the group consisting of polyvinylchloride, polytetrafluoroethylene, Dacron and a silicone polyurethane copolymer.

9. The medical article of claim 7 wherein the hydrophobic polymer in the treatment solution is a silicone-polyurethane copolymer.

10. The medical article of claim 7 wherein the medical article is fabricated from a silicone polymer.

11. The medical article of claim 6 wherein the medical article is fabricated from a hydrophobic polymer selected from the group consisting of polytetrafluoroethylene, Dacron, polyvinylchloride and a silicone polyurethane copolymer.

12. The medical article of claim 6 wherein the medical article is fabricated from a silicone polymer.

13. The medical article of claim 6 wherein the hydrophobic polymer in the treatment solution is a silicone-polyurethane copolymer.

14. The medical article of claim 6 which is a catheter.

15. The catheter of claim 14 which is an intravenous catheter.

16. The catheter of claim 15 which is fabricated from a biomedical silicone polymer.

* * * * *